US00PP20942P3

(12) United States Plant Patent
Glover

(10) Patent No.: US PP20,942 P3
(45) Date of Patent: Apr. 27, 2010

(54) APPLE TREE NAMED 'CAUFLIGHT'
(50) Latin Name: *Malus domestica borkh.*
Varietal Denomination: Cauflight

(75) Inventor: Stephen Glover, Kent (GB)

(73) Assignee: Pepinieres du Valois SARL, Villers-Cotterets (FR)

( * ) Notice: Subject to any disclaimer, the term of this patent is extended or adjusted under 35 U.S.C. 154(b) by 163 days.

(21) Appl. No.: 11/998,276

(22) Filed: Nov. 29, 2007

(65) Prior Publication Data

US 2009/0144865 P1 Jun. 4, 2009

(51) Int. Cl.
*A01H 5/00* (2006.01)

(52) U.S. Cl. ..... Plt./161
(58) Field of Classification Search ..... Plt./161
See application file for complete search history.

(56) References Cited

OTHER PUBLICATIONS

Upov Plant Variety Database 2008/05 p. 1.*

* cited by examiner

*Primary Examiner*—Annette H Para
(74) *Attorney, Agent, or Firm*—Michelle Bos

(57) ABSTRACT

A new apple tree named 'Cauflight' is described. 'Cauflight' is a mutation of 'Caudle' selected for its fruit, which has an intense bright red over color as compared to 'Caudle.'

6 Drawing Sheets

Latin name: *Malus domestica* borkh.
Variety denomination: 'Cauflight'.

BACKGROUND OF THE VARIETY

'Cauflight' is a new and distinct cultivar of apple tree *Malus domestica* Borkh. This new cultivar is a product of natural branch tree mutation of the variety 'Caudle' (U.S. Plant Pat. No. 9,068) discovered at Flightshott Farm, Kent, United Kingdom. 'Cauflight' is well characterized by its well defined dark red stripes over a bright red color. It is also characterized by its high percentage of colored fruits. Fruit was first observed in 2000, in an orchard situated at Flightshoot Farm in Kent, United Kingdom. Trees have since been propagated by budding in two different locations: Seiches sur le Loir, France and Villers-Cotterêts, France. The variety has been shown to remain true to type over successive generations in these two locations.

BRIEF DESCRIPTION OF THE VARIETY

'Cauflight' apple tree is similar to 'Caudle' in many respects, but is particularly distinguishable by its fruit, which has a bright red over color and a high percentage of highly colored fruit, particularly inside the tree (see FIG. 3). This characteristic of 'Cauflight' is desireable in that it leads to improved pack-out volumes as compared to 'Caudle' (see FIG. 5). The distinctive characteristics of 'Cauflight' are shown in Table 1 below.

TABLE 1

Comparison between 'Caudle' and 'Cauflight' fruits.

| Variety | Skin color | Amount of Overcolor | Pattern of Overcolor |
|---|---|---|---|
| Caudle | Light red (RHS 41A) | 50-75% | Strongly defined stripes |
| Cauflight | Bright red (RHS 45A) | 80-100% | Strongly defined stripes |

Tests have been conducted at Station Expérimentale de la Morinière, France, to compare 'Cauflight' and 'Caudle' at harvest time and after storage. Fruit taken from 4 year old trees were stored in controlled atmosphere: 0.5° C., 2.5% oxygen and 2% $CO_2$. Starch reversion, sugars, firmness and acidity were measured at harvest time and after storage. Results of these storage trials show that there is no significant difference in maturity between 'Caudle' and 'Cauflight' at harvest time. After storage, however, results show that level of sugar is higher for 'Cauflight'. These results are shown in Tables 2 and 3.

TABLE 2

Characteristics of 'Caudle' and 'Cauflight' at harvest time.

| Variety | Starch reversion (CTIFL code 1-10) | Sugar (% Brix) | Firmness ($kg/cm^2$) | Acidity (g/l) |
|---|---|---|---|---|
| 'Caudle' | 5.95 | 14.7 | 7.6 | 4.7 |
| 'Cauflight' | 6.33 | 14.6 | 7.55 | 4.8 |

TABLE 3

Characteristics of 'Caudle' and 'Cauflight' after 6 month CA storage.

| | Firmness ($kg/cm^2$) | | Sugars (% Brix) | | Acidity (g/l) | |
|---|---|---|---|---|---|---|
| Variety | After 24 hours | After 8 days | After 24 hours | After 8 days | After 24 hours | After 8 days |
| 'Caudle' | 6.6 | 6.0 | 14.8 | 14.5 | 3.3 | 3.0 |
| 'Cauflight' | 6.5 | 5.9 | 15.6 | 15.5 | 3.3 | 2.9 |

BRIEF DESCRIPTION OF THE PHOTOGRAPHS

DETAILED BOTANICAL DESCRIPTION OF THE VARIETY

Figure 1:
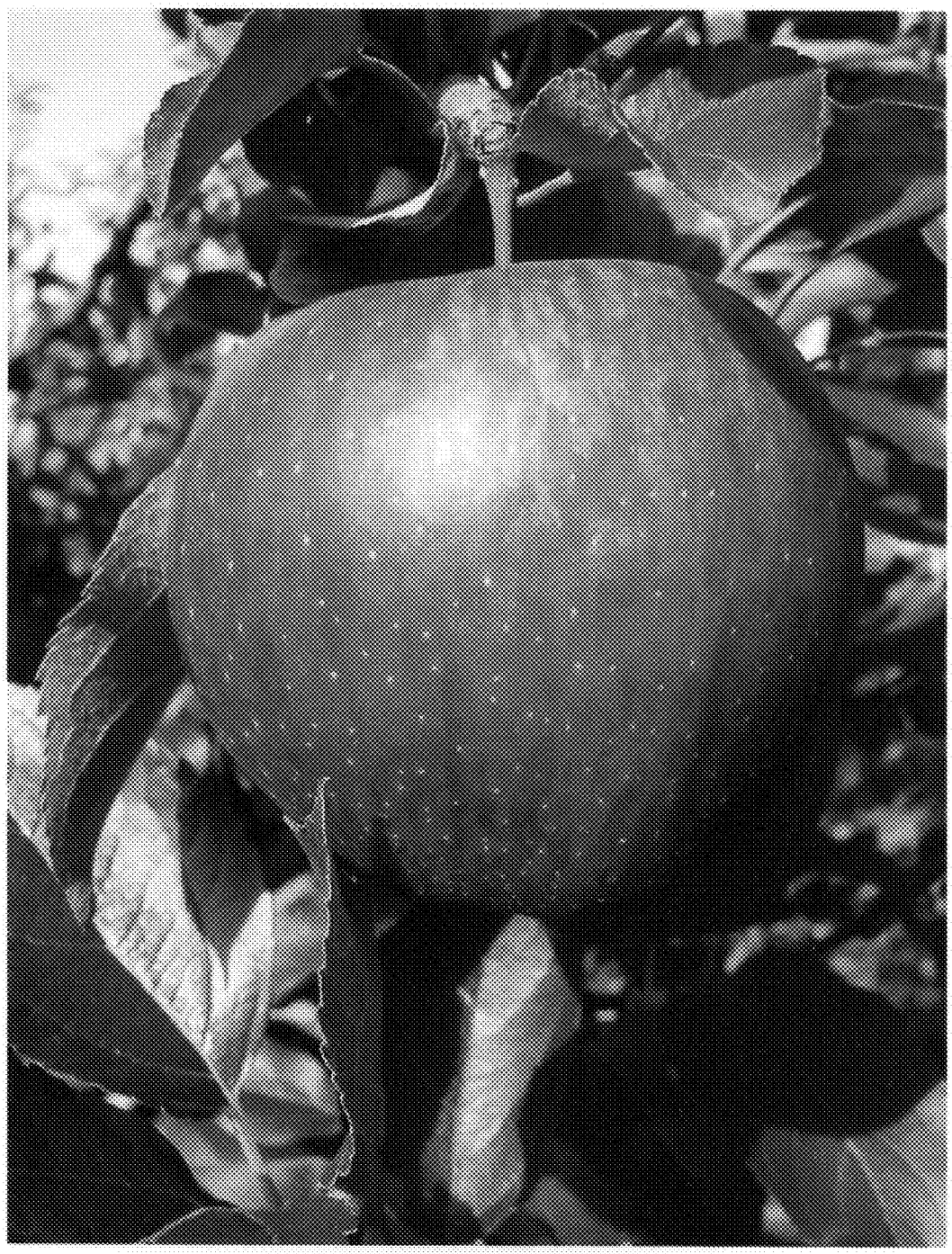
FIG. 1 shows fruit of 'Cauflight'.
Figure 2:
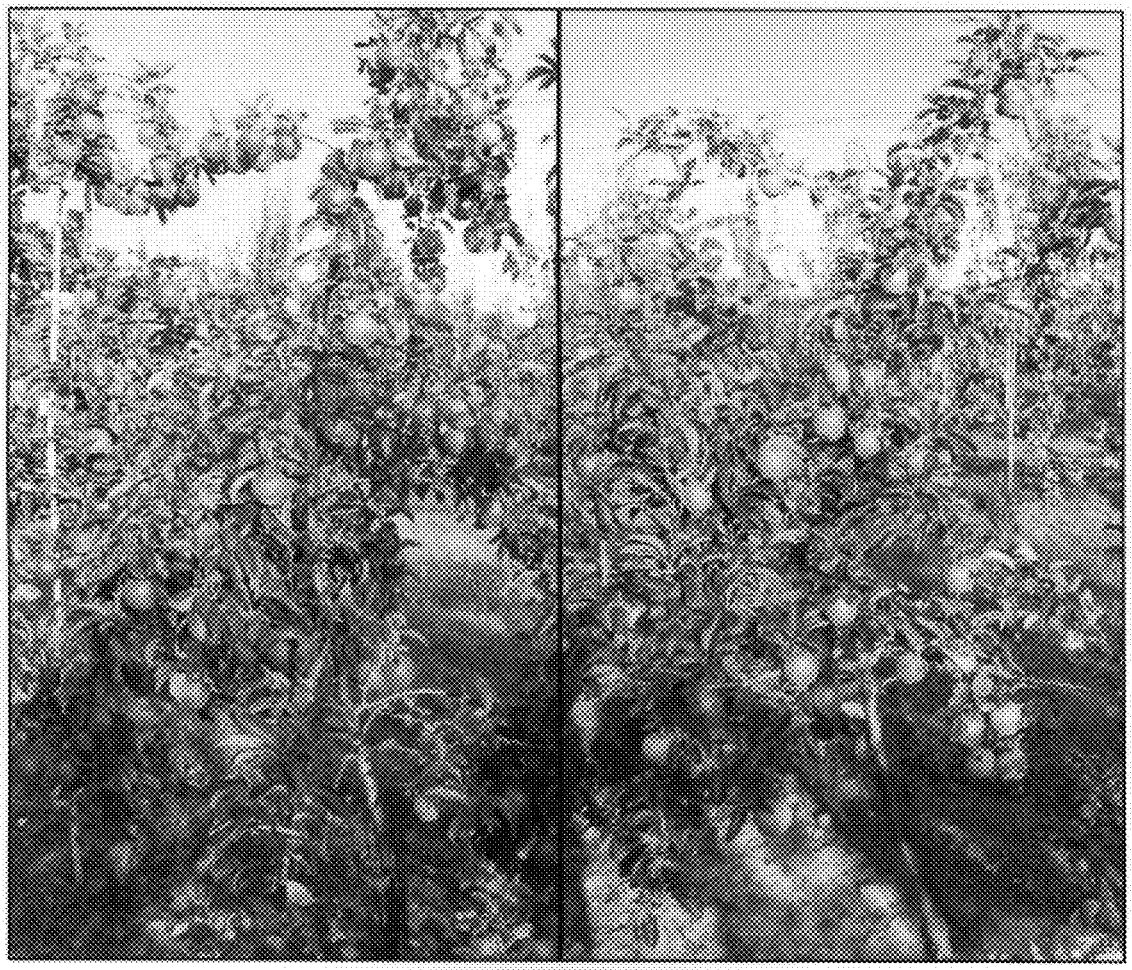
FIG. 2 shows 'Cauflight' tree (left) and 'Caudle' tree (right), 3 weeks before picking time.
Figure 3:
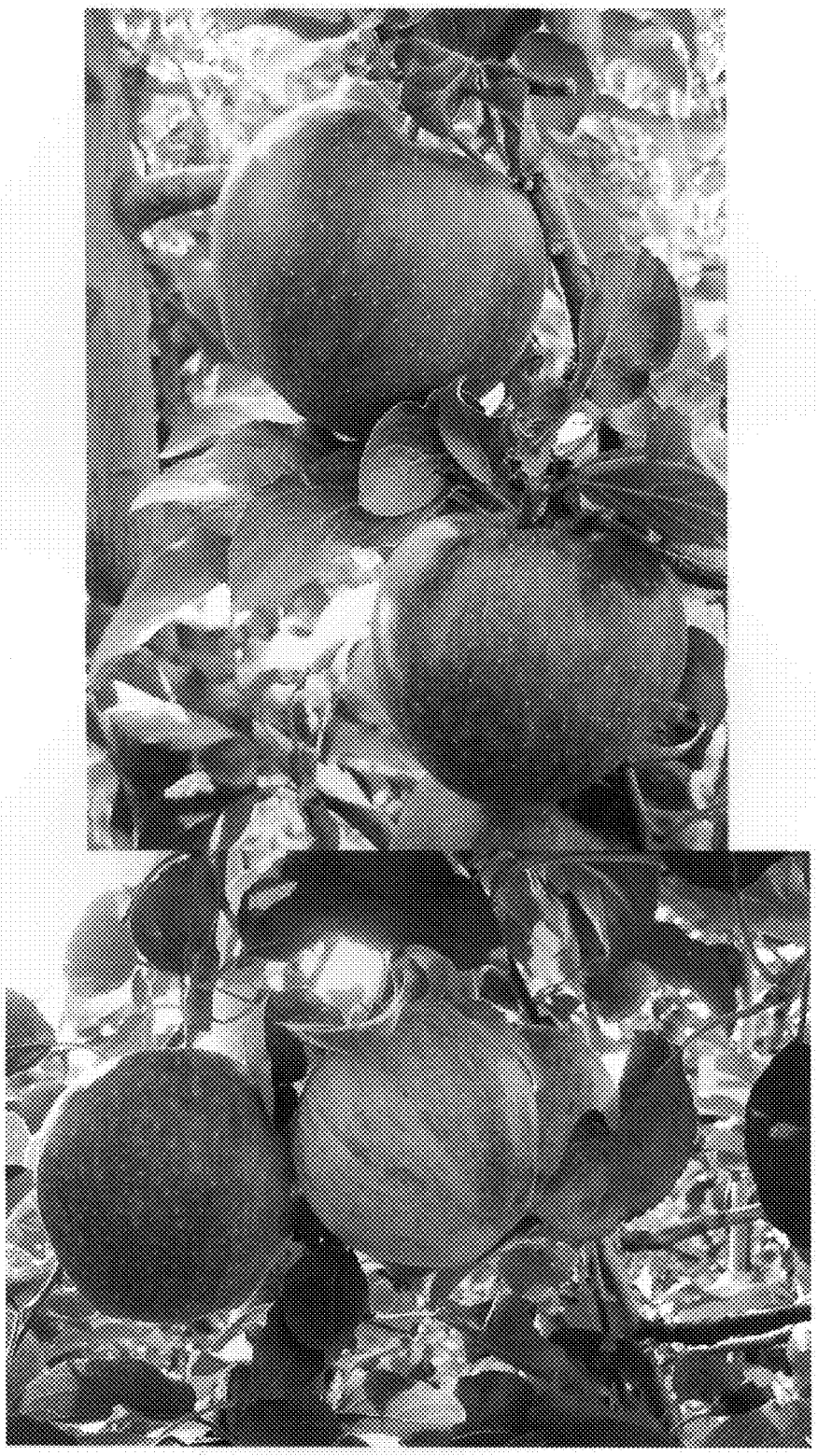
FIG. 3 shows 'Cauflight' fruit (above) and 'Caudle' fruit (below) on tree at picking time.
Figure 4:
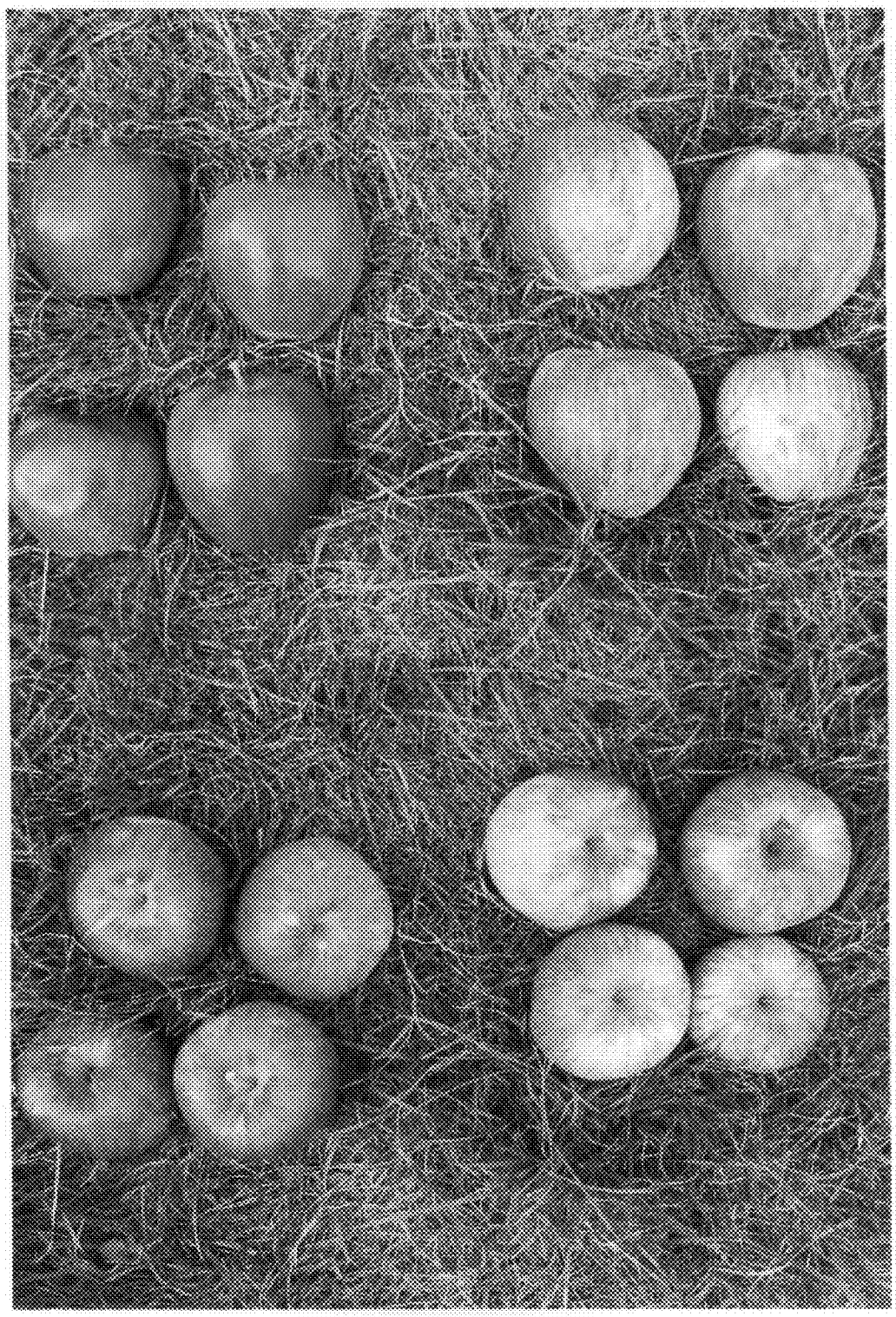
FIG. 4 shows 'Cauflight' fruit (left) and 'Caudle' fruit (right) at picking time.
Figure 5:
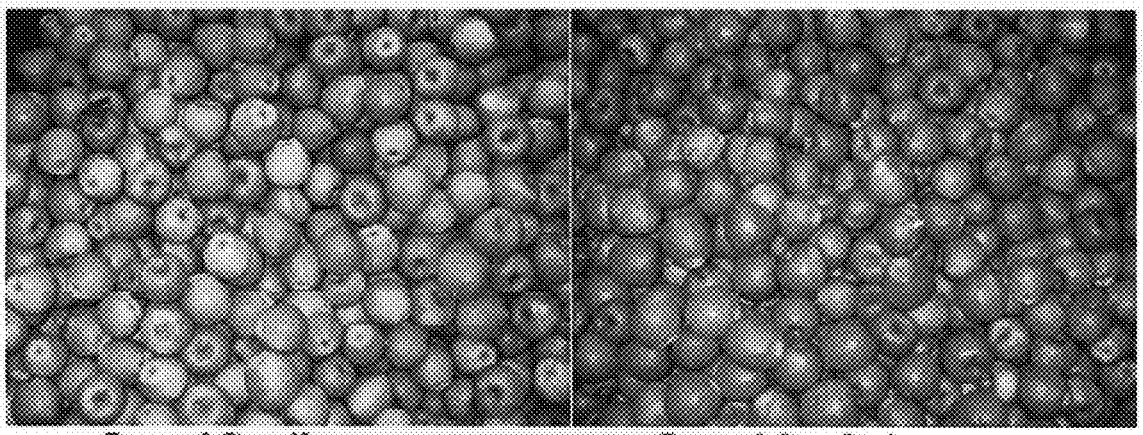
FIG. 5 shows a box of 'Cauflight' fruit (right) in comparison with box of 'Caudle' fruit (left)
Figure 6:
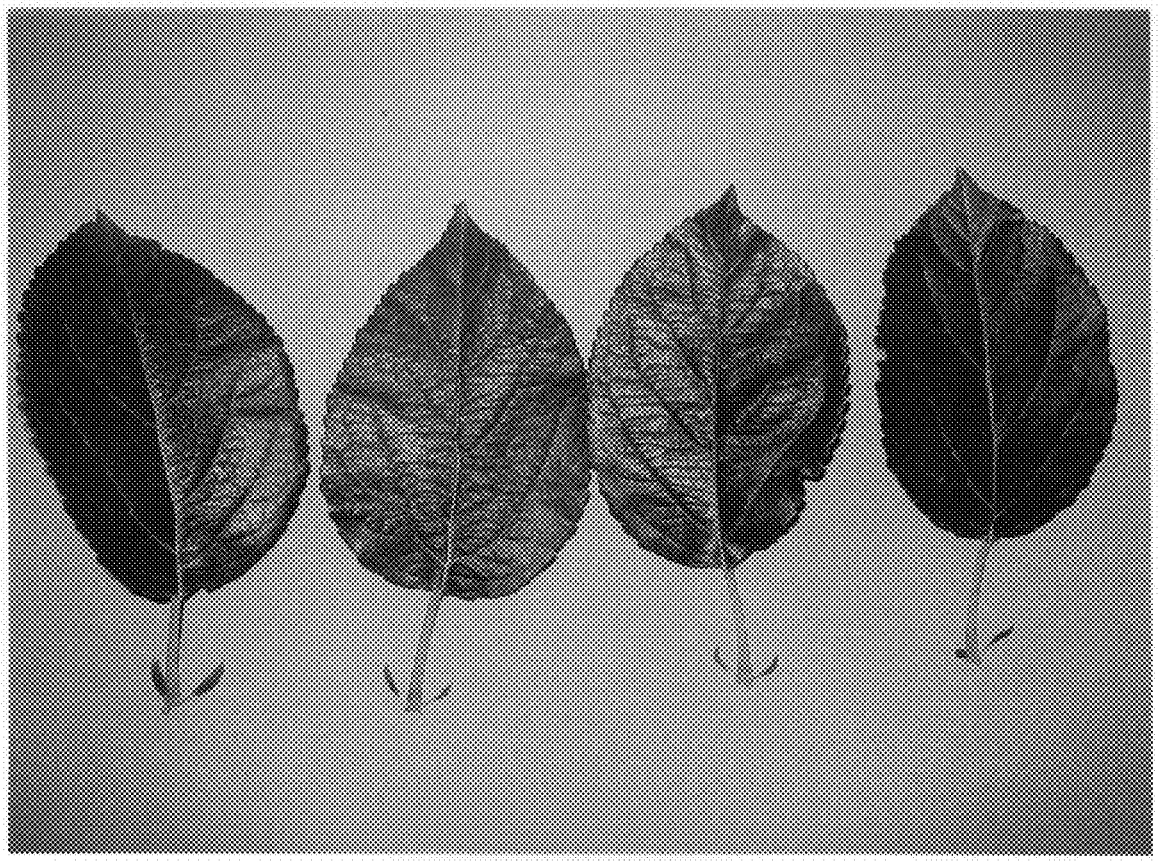
FIG. 6 shows leaves of 'Cauflight'.

The following detailed botanical description is based on observations made during the 2007 growing season at Seiches sur le Loir, France of six year old trees grown on Pajam 2 rootstock in high density plantings. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant, or any group of plants, of the new variety may vary from the stated average.

Tree: Vigor — medium (similar to 'Caudle'); Type — ramified; Habit — spreading; Height — 2.50 m; Trunk diameter (at 30 cm above the graft)—medium (avg. 45 mm), Bark texture — smooth to medium; Bark coloration — grey 187D.

Branch (fruiting branches located at about 1 m above the graft union): Length — medium (avg. 88 cm); Diameter — medium (avg.12 mm); Crotch angle 80° to 90° ; Bark color — purple-brown 166A.

Lenticels: Length — medium (avg. 31 mm); Pubescence — medium; Number of lenticels — medium to high (12 lenticels per $cm^2$).

Flower buds: Quantity per spur — 1 to 3; Shape — round to conical; Length — small to medium; Diameter — small to medium; Color — pink 63B.

Flowers: Color (flower buds) — pink 63B; Diameter of open flower — medium; Relative position of petal margin — overlapping; Number per cluster — 5 to 6; Date of first bloom — April 20 in Loire Valley, France (same as 'Golden Delicious'); Date of full bloom — April 25 in Loire Valley, France.

Petals: Number per flower — 5; Shape — ovoid; Length — medium; Width — medium; Apex — round; Base — conical-pointed; Margin — smooth; Coloration of upper surface — white N155C; Coloration of lower surface — light pink 65B.

Pistils: Size — medium; Color — yellow green N144C.

Stigma: Size — medium; Color — yellow green 150B.

Style: Size — medium; Color — yellow green 145A.

Ovary: Size — medium; Color — green 140A.

Anthers: Quantity — numerous; Size — medium; Presence of pollen — present; Color of pollen — yellow 3C.

Pedicel: Size — medium to long; Diameter — thin; Color — green 143B

Sepals: Quantity — 5; Coloration — green 143C; Shape — conical pointed.

Leaves: Shape — obtuse; Length (petiole not included) — medium-long (avg. 92 mm); Width — large (avg. 55 mm); Length/width ratio — medium (1.67); Blade margin — serrate; Apex — acuminate; Base shape — oblique; Color of upper surface — dark green 136A (in late summer); Color of lower surface — green 137C (in late summer); Attitude in relation to shoot — outwards.

Petiole: Length — long (avg. 33 mm); Diameter — medium (avg. 1.3 mm); Coloration — green 137C.

Fruit: Quantity per cluster — (2 to 3); Diameter — large (avg. 87 mm); Weight — heavy (avg. 250 g); Ratio of height to width — medium (1.06); General shape in profile — rounded to conical; Position of maximum diameter — in middle; Ribbing — medium; Crowning at calyx end — strong; Size of eye — large (avg. 21.3 mm); Aperture of eye — partially open; Length of sepal — medium (avg. 6 mm); Bloom of skin — weak; Greasiness of skin — very weak; Background color of skin — yellow 7D; Over color of skin — red 45A; Amount of over color — 80% to 100%; Intensity of over color — strong; Pattern of over color — solid stripes with flush; Amount of russet around stalk cavity — low; Amount of russet on cheeks — absent; Area of russet around eye basin — absent or very weak; Length of stalk — long (avg. 32.8 mm); Thickness of stalk — medium to large (avg. 2.4 mm); Depth of stalk cavity — deep (avg. 21.4 mm); Width of stalk cavity — medium (avg. 26.4 mm); Depth of eye basin — medium (avg. 13.4 mm); Width of eye basin — medium (avg. 23 mm); Firmness of flesh — firm; Flesh texture — medium to fine; Aroma — moderately aromatic and sweet; Juiciness — medium to high; Brix — 12° brix minimum at harvest time; Flesh coloration — light yellow 4D; Stem coloration — brown 199A.

Seeds: Quantity per fruit — 5 on average; Shape — truncate ovoid; Coloration — dark brown 165A.

Harvest: Time for harvest — late, beginning of October (similar to Braeburn); Number of picks — three picks; Amount of fruit produced per tree per harvest — 120 fruits on fifth-leaf trees.

Disease resistance/susceptibility: None noted.

I claim:

1. A new and distinct apple tree substantially as described and illustrated herein.

* * * * *

*Box of Caudle* *Box of Cauflight*